United States Patent [19]

Sagstetter et al.

[11] Patent Number: 5,120,311
[45] Date of Patent: Jun. 9, 1992

[54] BLOOD COLLECTION TUBE HOLDER

[75] Inventors: William E. Sagstetter, Denver; John E. Cooke, Lakewood; Louis E. Greenberg, Denver; Alan A. Wanderer, Englewood, all of Colo.

[73] Assignee: Medical Safety Products, Inc., Denver, Colo.

[21] Appl. No.: 430,311

[22] Filed: Nov. 1, 1989

[51] Int. Cl.⁵ ............................................. A61M 5/00
[52] U.S. Cl. ................................ 604/110; 604/187; 604/197; 604/198; 604/232; 128/763
[58] Field of Search ............... 604/187, 197, 198, 199, 604/232; 128/763

[56] References Cited

U.S. PATENT DOCUMENTS

| | | | |
|---|---|---|---|
| 4,592,744 | 6/1986 | Jagger | 604/192 |
| 4,752,290 | 6/1988 | Schramm | 604/198 |
| 4,758,231 | 7/1988 | Haber et al. | 604/198 |
| 4,790,827 | 12/1988 | Haber et al. | 604/198 |
| 4,813,426 | 3/1989 | Haber et al. | 128/763 |
| 4,834,718 | 5/1989 | McDonald | 604/198 X |
| 4,840,185 | 6/1989 | Hernandez | 128/763 |
| 4,900,310 | 2/1990 | Ogle, II . | |

Primary Examiner—Robert Bahr
Assistant Examiner—J. Doyle
Attorney, Agent, or Firm—Cahill, Sutton & Thomas

[57] ABSTRACT

An insert for supporting a double ended needle during a blood collection procedure is translatably mounted within a cylinder for retracting the anterior needle into the cylinder on completion of the procedure to prevent needle stick while the posterior needle remains continually shielded against needle stick by the insert. An anterior lock position stabilizes the double ended needle during the blood collection procedure and a posterior lock position retains both ends of the needle shielded. A ramp may be associated with the posterior lock position to prevent further translation of the insert and reuse of the holder. For a reusable holder embodiment, the used double ended needle is retracted, safely enclosed and locked inside the cylinder. The anterior end of the cylinder is adapted for receiving the open end of a conventional needle shield to permit gripping of the needle supporting hub and disengagement of the needle from the insert without exposure to needle stick. A replacement needle may then be mounted in the insert and the holder reused.

63 Claims, 3 Drawing Sheets

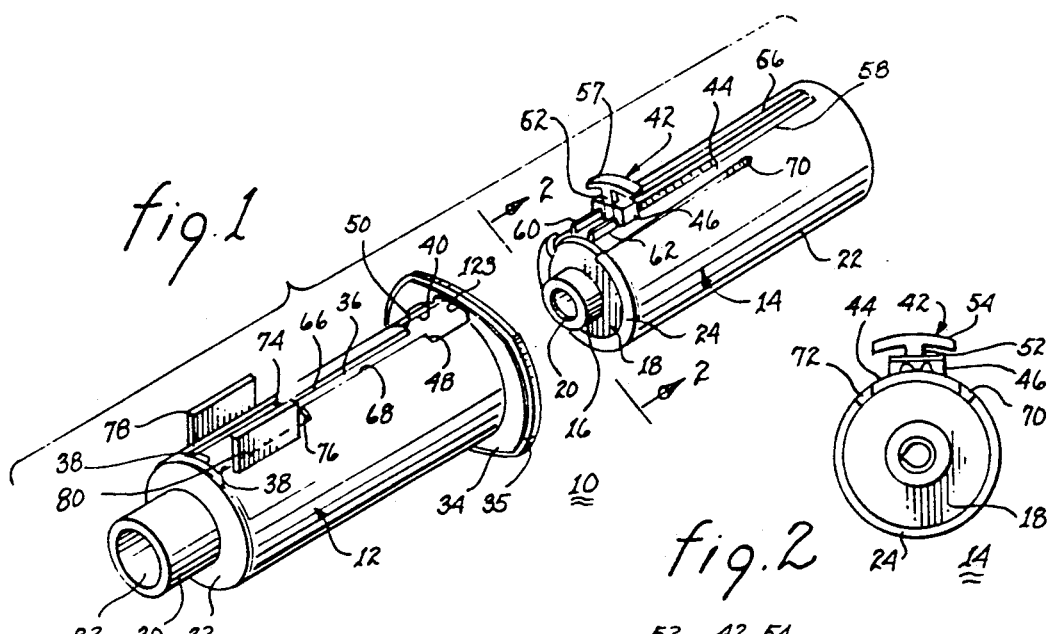
fig. 1
fig. 2
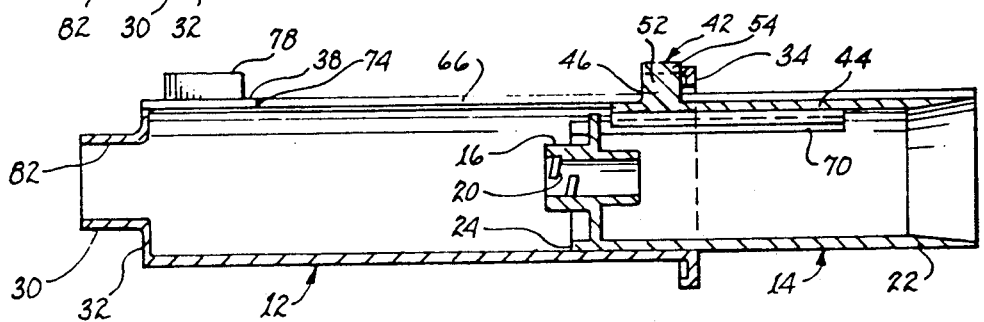
fig. 3
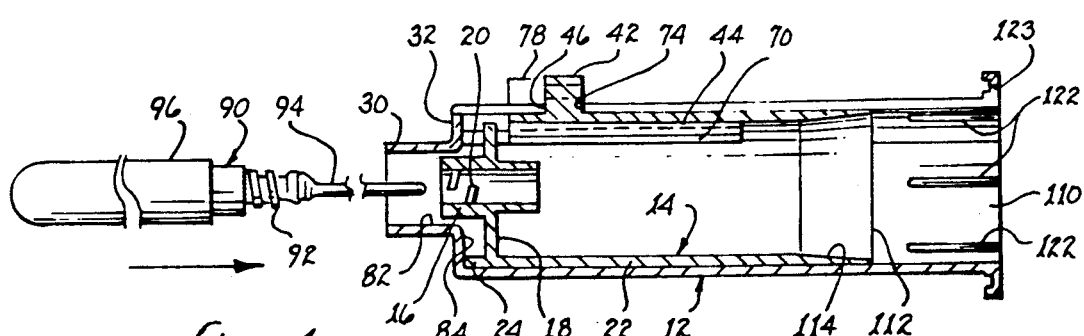
fig. 4
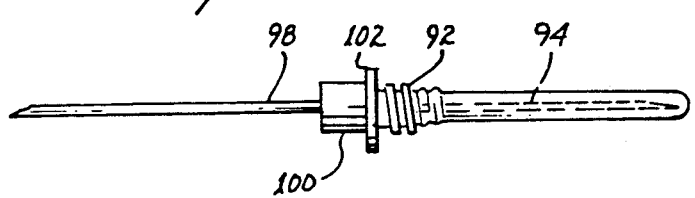
fig. 5

BLOOD COLLECTION TUBE HOLDER

BACKGROUND OF THE INVENTION

1. Field of the Invention

The present invention relates to blood collection tube holders for use during a blood collection procedure and, more particularly, to a holder having a needle supporting insert translatable with a cylinder for shielding both ends of a double ended needle after use to prevent inadvertent needle stick.

2. Description of the Prior Art

Conventional blood collection procedures involve venipuncture to draw blood into a blood collection tube. The conventional double ended needle includes a hub having an anterior needle extending in one direction and a posterior needle extending in the other direction. The hub is threadedly engaged with an apertured threaded end of a barrel to locate the posterior needle within the barrel. The other end of the barrel is open to receive an evacuated blood collection tube having a stopper to penetrably receive the posterior needle. Upon venipuncture, the blood will flow through the needle into the blood collection tube. After at least partial fill of the blood collection tube, it may be replaced by one or more further evacuated blood collection tubes, depending upon how many samples of blood are to be drawn.

On completion of the procedure, the anterior needle is withdrawn from the patient. The manner of disposal of the needle varies, depending upon the phlebotomist, the procedures to be followed and other considerations. Whether the needle is immediately capped with a needle shield for later disposal, whether the barrel is immediately disposed with the exposed needle attached or whether the needle is immediately detached or replaced, a substantial risk of inadvertent needle stick exists.

Many incurable or fatal diseases are transmissible through contact with the blood of an infected person. A needle used during a blood collection procedure obviously contains a quantity of blood. In the event of needle stick, infection from infected blood is highly likely. Considering that inadvertent needle stick occurs frequently, the degree of exposure of medical personnel to incurable or fatal diseases is intolerably high.

Particularly in recent years, various devices have been developed to minimize the likelihood of inadvertent needle stick. These devices generally include mechanisms for shielding the anterior needle after a blood collection procedure. Many of these devices perform the function of minimizing the likelihood of inadvertent needle stick but suffer from other drawbacks. Some of the devices require a two handed operation which renders such devices unacceptable since a phlebotomist must have one hand free to perform blood collection related functions. Some of the devices are relatively complex which renders their cost too high to be acceptable to medical facility administrators, particularly if such devices are not reusable. Yet other blood collection devices are complex to operate and require substantial training in proper manipulation. Such training is difficult and expensive to implement and there exists a general resistance to adaptation or modification of existing procedures, despite an understanding of increased safety which would result.

SUMMARY OF THE INVENTION

A blood collection tube holder for use in a blood collection procedure includes an insert having one end threadedly engagable with the hub of a double ended needle. The other end of the insert is configured to receive a conventional blood collection tube for penetrable engagement with the posterior needle of the double ended needle. The insert is axially translatable within a cylinder having a collar at one end for translation of the anterior needle of the double ended needle therethrough. A leaf spring biased tab extends radially from the insert for penetrable engagement with two detent positions disposed in the cylinder and interconnected with an axially aligned slot. Translation of the tab from one detent position to the other will exteriorize or retract the anterior needle through the collar. For a single use holder, a guard in conjunction with the detent position corresponding to retraction of the anterior needle will prevent further manipulation of the tab and prevent exteriorization of the anterior needle. For a reusable holder, the collar is apertured to accommodate insertion of a conventional needle shield to permit housing of the anterior needle within the cylinder while the needle is safely enclosed and locked within the holder. Engagement of the shield with the needle hub will permit disassociation of the needle hub from the insert and accommodate withdrawal of the covered double ended needle. Accordingly, the holder can permit one handed retraction of the anterior needle on completion of the blood collection procedure to preclude inadvertent needle stick. In the reusable configuration of the holder, the needle can be removed and replaced without exposing medical personnel to the possibility of needle stick during such removal and replacement.

It is therefore a primary object of the present invention to provide a blood collection tube holder for retracting and shielding a double ended needle after completion of a blood collection procedure.

Another object of the present invention is to provide a blood collection tube holder which precludes needle stick and is sufficiently inexpensive to permit one time use.

Still another object of the present invention is to provide a reusable blood collection tube holder which reduces cost per blood collection procedure and precludes inadvertent needle stick subsequent to a blood collection procedure and during replacement of a double ended needle.

Yet another object of the present invention is to provide a wobble free inexpensive double ended needle supporting insert axially translatable within a cylinder to shield the needle against inadvertent needle stick.

A further object of the present invention is to provide a safe method for shielding the anterior and posterior needles of a double ended needle subsequent to a blood collection procedure.

A yet further object of the present invention is to provide a difficult to disassemble compact blood collection tube holder for precluding inadvertent needle stick.

A still further object of the present invention is to provide a reusable blood collection tube holder for precluding inadvertent needle stick during recapping and replacing a double ended needle.

A still further object of the present invention is to provide a method for replacing a double ended needle in a blood collection tube holder while precluding possibility of inadvertent needle stick.

A still further object of the present invention is to provide a blood collection tube needle holder adapted to accept and use a plurality of different length double ended needles and blood collection tubes.

These and other objects of the present invention will become apparent to those skilled in the art as the description thereof proceeds.

BRIEF DESCRIPTION OF THE DRAWINGS

The present invention will be described with greater clarity and specificity with reference to the following drawings, in which:

FIG. 1 is an isometric view illustrating the cylinder and the insert of a blood collection tube holder;

FIG. 2 is an end view taken along lines 2—2, as shown in FIG. 1;

FIG. 3 is a cross sectional view illustrating the insert in the retracted position;

FIG. 4 is a cross sectional view illustrating the insert in the extended position for receiving a double ended needle;

FIG. 5 is a side view of a representative conventional double ended needle;

DESCRIPTION OF THE PREFERRED EMBODIMENT

Figure 6:
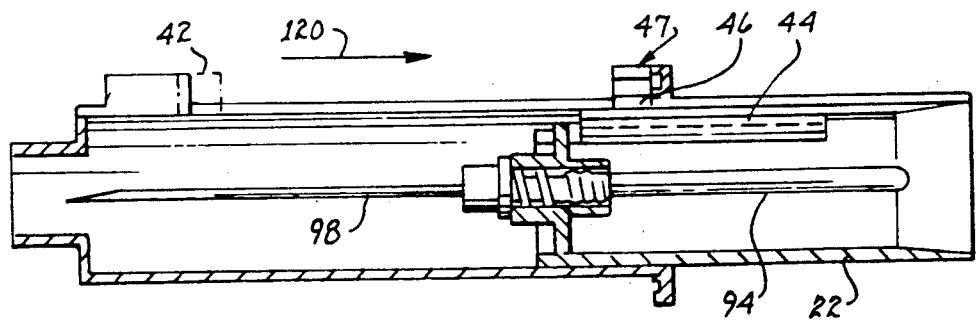
FIG. 6 illustrates retraction of the needle supporting insert.

Any implement or device used in a medical procedure must satisfy certain federally imposed criteria. To be saleable and therefore used, further, sometimes obvious and sometimes subtle, criteria also must be met. The latter criteria is sometimes the most difficult to satisfy since it relates to perceptions held by the affected medical community of what the device should or should not be. Furthermore, any replacement device for an element used in an existing procedure should require minimal, if any, training in its use in order for it to be embraced and accepted by the ultimate users. Finally, in the area of routine procedures, operative advantages, safety benefits or time-motion benefits may be insufficient to override even small cost increases due to the usually fixed charges for such routine procedures. Venipuncture procedures for filling blood collections tubes are undertaken daily, sometimes hundreds of times, in every physician's office, clinic and hospital. The associated training and procedures have been established and stabilized for many years. The charge for this procedure is relatively fixed and little variation due to higher equipments costs is possible. Accordingly, any blood collection tube holders developed for use in such procedure must provide advantages over existing devices of sufficient magnitude to warrant adoption of a new device and the costs of the new device must be commensurate with existing costs.

Referring jointly to FIGS. 1 and 2, a two part blood collection tube holder 10 for detachably supporting the hub of a double ended needle is shown. The holder includes a cylinder 12 for axially translatably supporting an insert 14. The insert includes a hollow internally threaded boss 16 extending axially from closed end 18 of insert 14. Threads 20 in the boss are engagable with the conventional threaded hub of a double ended needle and, through such threaded engagement, firmly supports the needle. The insert includes a posteriorly extending generally cylindrical skirt 22. The axial length of the skirt is configured sufficient to house the posterior needle therein and guard against inadvertent needle stick from the posterior needle. A segment of an axially oriented annular ridge 24 extends anteriorly from closed end 18.

Cylinder 12 is generally cylindrical in configuration and includes a hollow collar 30 extending anteriorly from an annular flange 32 disposed at the anterior end of the cylinder. A retaining finger flange 34 extends radially from the posterior end of cylinder 12; this finger flange may include a ridge 35 extending along the perimeter.

An axially aligned slot 36 extends between a first circumferentially expanded slot segment 38 and a second circumferentially expanded slot segment 40. Insert 14 includes a tab 42 located generally at the anterior end of a leaf spring 44 formed as part of skirt 22. Upon mating of insert 14 with cylinder 12, tab 42 extends through slot 36 and expanded slot segments 38,40 as a function of the translational position of the insert with respect to the cylinder. To facilitate thumb access to tab 42 during exteriorization of the anterior needle in the reusable configuration of holder 10, the upper edges of wing 34 extending laterally in opposed directions from expanded slot segment 40 may be cut down or scalloped below the height of the tab.

Referring jointly to FIGS. 1-3, insert 14 is illustrated in the needle retracted position with respect to cylinder 12. Tab 42 includes a base 46 having a lateral width approximately equivalent to the circumferential spacing of expanded slot segments 38,40. The height of the base is equal to or greater than the thickness of cylinder 12 adjacent expanded slot segments 38,40. Accordingly, the anterior edge of the base will bear against anterior edges 48,50 of expanded slot segment 40 and preclude anterior movement of the tab. Thereby, insert 14 is positionally locked with respect to cylinder 12 in the needle retracted position illustrated. A pedestal 52 extends upwardly from base 46 to support wing 54 of the tab. The lateral width of the pedestal is commensurate with the width of slot 36 to accommodate translation of the pedestal along the slot. Wing 54 extends in opposed directions from pedestal 52 a sufficient distance to prevent depression of tab 42 radially inwardly of cylinder 12, whether the tab is within slot 36, expanded slot segment 38 or expanded slot segment 40. Upon depressing tab 42 radially inwardly, resulting in radial inward bending of leaf spring 44, pedestal 52 is brought into engagement with slot 36. Upon such engagement, the tab is translatable axially along the slot resulting in commensurate rectilinear motion of insert 14. To stabilize axial translation of insert 14 within cylinder 12, a pair of axially aligned ridges 56,58 extend posteriorly from tab 42 along the leaf spring. A similar pair of ridges 60,62 may extend anteriorly of tab 42. The circumferential width defined by pair of ridges 56,58 and 60,62 is commensurate with the circumferential width between edges 66,68 of slot 36. Accordingly, the two pairs of ridges, in combination with the edges of the slot, minimize rotation about the longitudinal axis of insert 14 with respect to cylinder 12. The degree of springiness provided by leaf spring 44 is a function of, not only the material of skirt 22 of insert 14, but of the length of slots 70,72 defining the lateral edges of the leaf spring.

To translate insert 14 anteriorly with respect to cylinder 12, tab 42 is depressed radially inwardly to engage pedestal 52 with slot 36. Upon anterior translation of the tab, base 46 will ultimately become coincident with expanded slot segment 38. Upon such coincidence, the upward force exerted by leaf spring 44 will cause the base to penetrably engage anterior expanded slot segment 38. In this position, posterior axial translation of insert 14 is precluded by the rear edge of the base engaging posterior edges 74,76 of expanded slot segment 38, as illustrated in FIG. 4.

To discourage inadvertent depression of tab 42 while it is in locked engagement with expanded slot segment 38, a pair of walls 78,80 may be incorporated on opposed sides of the expanded slot segment. These walls are of a height and width commensurate with the height and width of tab 42 when the latter is in locked engagement with expanded slot 38. These walls will have the effect of shielding the tab and guarding against inadvertent depression of the tab with a resulting release of the tab from the expanded slot segment, yet access to the tab to deliberately depress it is not impeded.

Collar 30 defines a passageway 82 of sufficient diameter to accommodate partial penetration by boss 16, as shown in FIG. 4. The positional rigidity of boss 16 at the anterior end of cylinder 12 is provided by a combination of factors. First, ridge 24 of skirt 22 bears against inner surface 84 of annular flange 32 and is positionally maintained thereagainst by base 46 of tab 42 bearing against edges 74,76. Thereby, longitudinal stability of the insert with respect to the cylinder is provided. Second, the diameter of the anterior end of insert 14 proximate ridge 24 is in close tolerance with the internal anterior diameter of cylinder 12 proximate annular flange 32 to prevent lateral movement therebetween.

Segmented annular ridge 24 serves three main functions. First, it displaces the tab posteriorly to accommodate a small angle of penetration during venipuncture. Second, it displaces the contact point between the posterior needle and the blood collection tube posteriorly to provide greater gripping surface upon the blood collection tube. Third it enhances the longitudinal surface area between the insert and the cylinder.

A conventional commercially available double ended needle 90 having a threaded hub 92 is used with holder 10. To secure double ended needle 90 to holder 10, the conventional shield protecting posterior needle 94 and its associated valve is removed. Such removal will expose threaded hub 92. The posterior needle is inserted through collar 30 and boss 16 to threadedly engage the needle hub with threads 20 within the boss. The hub of the double ended needle includes an anterior needle shield support structure 100 terminated by a radially extending flange 102 for supporting a conventional shield 96. Just prior to venipuncture, shield 96 is disengaged from support structure 100 and removed to expose anterior needle 98 (see FIG. 5).

As part of the blood collection procedure, a blood collection tube having a needle penetrable stopper is inserted through the open posterior end 110 of cylinder 12, through open posterior end 112 of insert 14 and into penetrable engagement with posterior needle 94. To assist and ease insertion of the blood collection tube within insert 14, the inside surface of posterior end 112 may be formed as an annular ramp 114.

On completion of the blood collection procedure and withdrawal of the last blood collection tube, a phlebotomist or other medical personnel can hold cylinder 14 in the palm of the hand and lightly grasp the cylinder with the fingers. The thumb can be used to depress tab 42 and thereafter crook the thumb to draw the tab posteriorly, as illustrated by arrow 120 in FIG. 6. The posterior movement of tab 42 will result in commensurate movement of insert 14 with respect to cylinder 12. When base 46 of tab 42 comes into correspondence with expanded slot segment 40, leaf spring 44 will urge upward movement of the tab to bring base 46 into engagement with the expanded slot segment. In the resulting position of insert 14, anterior needle 98 will have been drawn completely into the interior of cylinder 12. In this position of the anterior needle, inadvertent needle stick by the anterior needle will be impossible. The axial length of insert 14 is greater than the length of posterior needle 94 and the posterior needle will be contained completely therewithin. Thereby, inadvertent needle stick from posterior needle 94 will also be precluded by the shielding effect of skirt 22, as depicted in FIG. 6.

For manufacturing reasons, the interior surface of cylinder 12 tapers radially outwardly posteriorly. Such tapering will permit some radial movement of the anterior end of insert 14 when the insert is in the needle retracted position shown in FIG. 6. To maintain anterior needle 98 generally coincident with the longitudinal axis of cylinder 12, a plurality of tapered longitudinally extending ridges 122 are disposed internal to the posterior end of cylinder 12, as depicted in FIG. 4. A plurality of these ridges, such as 6, equiangularly spaced about cylinder 12, reduce the effective diameter of the cylinder at its posterior end into general conformance with the exterior diameter of the anterior end of insert 14. Thereby, the anterior end of insert 14 is positionally stabilized by the ridges to prevent wobble and misalignment of anterior needle 98 with the longitudinal axis of cylinder 12. Necessarily, the dimensional intrusion of tapered ridges 122 must be commensurate with the difference in diametric dimension between the posterior internal end of cylinder 12 and the external diameter of the anterior end of insert 14. Alternatively or in conjunction with ridges 122, the radial exterior of ridges 56,58 can be increased proximate tab 42 to bring about contact with arch 123 in finger flange 34 upon posterior displacement of insert 14. The resulting physical contact will reduce the likelihood of wobble and maintain the anterior needle axially aligned with the cylinder.

Accordingly, in the needle retracted position shown in FIG. 6, the axial position of insert 14 with respect to cylinder 12 is stabilized by engagement of tab 42 with expanded slot segment 40. Radial stability, to prevent wobble, between the insert and the cylinder is provided by the plurality of tapered ridges engaging the circumferential surface of the anterior end of insert 14. This stability is important for two primary reasons. First, it permits aligned reextension of anterior needle 98 through passageway 82 of collar 30. Second, as will be described below, it permits capping of anterior needle 98 by sliding a needle shield through passageway 82 to cover the anterior needle.

Figure 7:
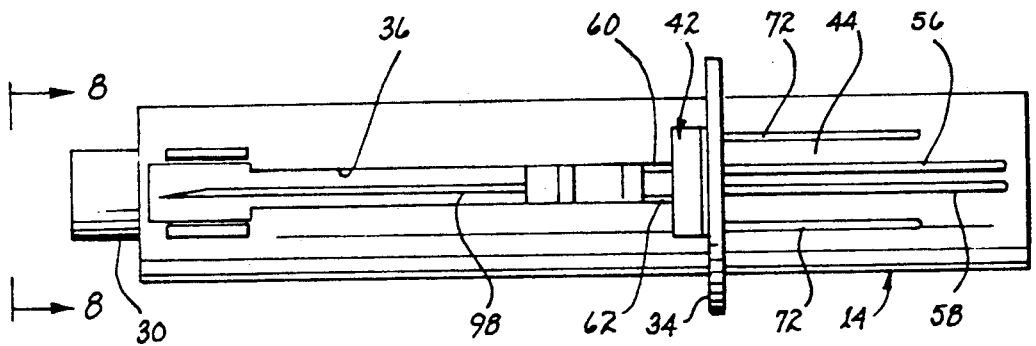
FIG. 7 is a top view illustrating the insert in the fully retracted position.
Figure 8:
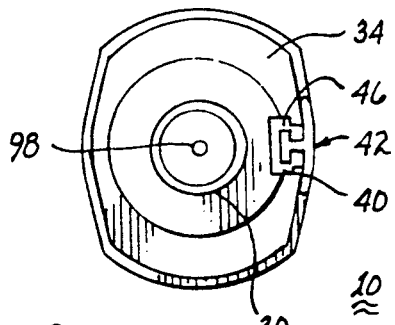
FIG. 8 is an end view taken along lines 8—8, as shown in FIG. 7.

Referring jointly to FIGS. 7 and 8, there is shown a top view of holder 10 and an end view thereof. These views clearly illustrate leaf spring 44 extending anteriorly as part of insert 14 and defined by slits 70,72. Tab 42 has been brought posteriorly adjacent finger flange 34 to position anterior needle 98 in the retracted position. Ridges 56,58 extending radially outwardly from leaf spring 44 slidably engage slot 36, as depicted by anterior extensions 60,62 of these ridges. In the retracted position, base 46 of tab 42 is lockingly engaged within expanded slot segment 40 to preclude anterior translation of insert 14 without an accompanying depression of tab 42 to disengage the base from the expanded slot segment. As particularly noted in FIG. 8, needle 98 is essentially axially centered with passageway 82 of collar 30.

Figure 9:
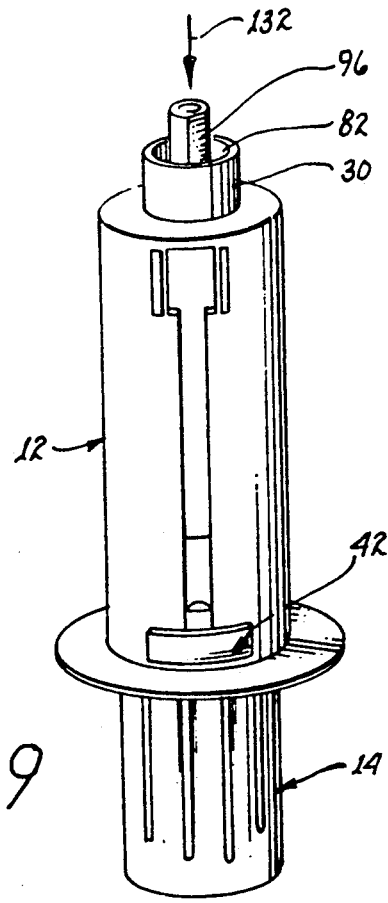
FIG. 9 illustrates insertion of a needle shield to shield the anterior needle contained within the holder held vertically.
Figure 10:
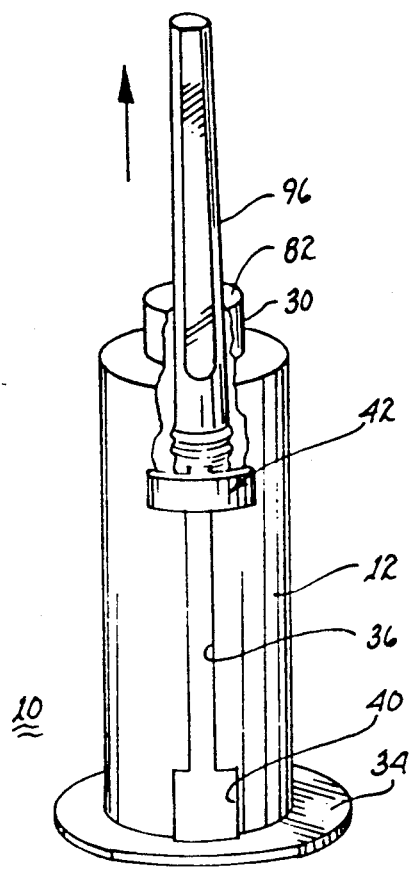
FIG. 10 illustrates steps for replacing a double ended needle.

After completion of a blood collection procedure, holder 10 may be discarded or the holder may be reused with a replacement needle. To replace the double ended needle, a standard conventional anterior needle shield used as part of the packaging for the double ended needle is used. The open end of shield 96 is inserted through passageway 82 into cylinder 12 while tab 42 is locked in expanded slot segment 40. Continued downward movement of the shield, as depicted by arrow 132 shown in FIG. 9, will ultimately enclose the needle and the shield will come into engagement with support structure 100 of the hub of the double ended needle. For most commercially available double ended needles, the engagement of the shield with the hub is a simple press fit. At this point, a user has two options for removing the double ended needle. First, shield 96, after engaging the hub of the double ended needle, can be rotated to bring about threaded disengagement between the hub and boss 16 of insert 14. Upon such disengagement, shield 96 is withdrawn and the anterior needle will be lodged therein. Secondly, as depicted in FIG. 10, tab 42 may be translated anteriorly to extend shield 96 and the enclosed needle. With such extension, a greater gripping area of the shield will be available for a user. Accordingly, extension of the shield prior to threaded disengagement of the double ended needle from boss 16 may be more facile. After removal of the double ended needle, the posterior needle may be capped with the shield initially supplied with the double ended needle. Such capping is performed by holding shield 96 to stabilize and positionally maintain the posterior needle during capping. Holder 10 is now ready to receive a replacement needle. Collar 30 may be adapted diametrically to receive and seat the proximal end of the shield in preparation for penetration and lodgment of the anterior needle within the shield.

Figure 12:
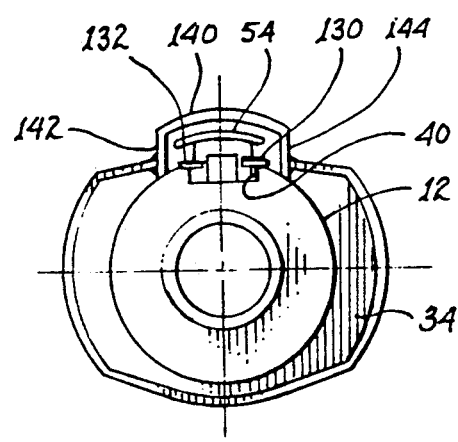
FIG. 12 is an end view taken along lines 12—12, as shown in FIG. 11.
Figure 11:
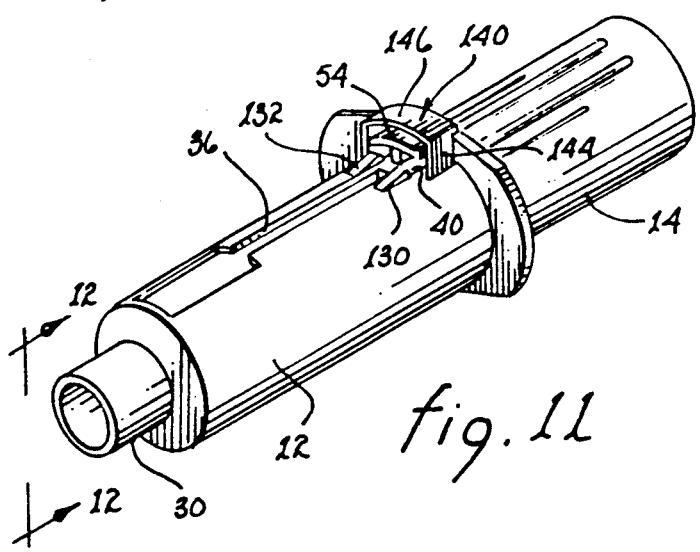
FIG. 11 illustrates a one time use embodiment of the holder shown in FIG. 1.

Under certain circumstances, it may be preferable to preclude reuse of holder 10. Such reuse can be precluded by rendering tab 42 inaccessible upon placement of the tab within expanded slot segment 40. Referring to FIGS. 11 and 12, there is illustrated a guard 140 usable for this purpose. Side walls 142,144 extend outwardly from cylinder 12 at opposed sides of expanded slot segment 40. A cover 146 interconnects the upper edges of the side walls at a location just above wing 54 of tab 42. The side walls and cover extend anteriorly from wing 34 a sufficient distance to totally enclose the tab.

When tab 42 is drawn posteriorly during retraction of the double ended needle, it will slide into guard 140. Upon entering within the guard, base 46 of the tab will become coincident with expanded slot segment 40 and due to spring action of leaf spring 44, the tab will pop up into close proximity with cover 146. In this position, the tab will be difficult to access and without extraordinary measures, the retracted double ended needle cannot be extended. Accordingly, the configuration of holder 10 illustrated in FIGS. 11 and 12 provides a non reusable blood collection tube holder. To augment difficulty in withdrawing tab 42 from within guard 140, a pair of ramps 130,132 can be formed on cylinder 12. These ramps are disposed on opposed sides of slot 36 and extend toward and terminate at anterior edges 48,50 of expanded slot segment 40. The height of these ramps permits travel thereover of wing 54 during posterior travel of tab 42. Under certain circumstances, a single ramp on one side of slot 36 may be adequate. The locking feature of the ramps operates as follows. To reposition tab 42 anteriorly, the tab must be depressed to disengage, radially inwardly, base 46 from expanded slot segment 40. Such depression of the tab will lower wing 54 to a location against the butt end of the ramps. The butt end of the ramps will interfere with anterior relocation of tab 42 and the tab becomes mechanically locked within guard 140.

Cylinder 12 and insert 14 of holder 10 are manufacturable relatively inexpensively through use of molds. After manufacturing, the holder must be assembled. Such assembly is relatively easily performed in the following manner. The anterior end of leaf spring 44 of insert 14 is depressed sufficiently to permit insertion of the insert and tab within the open posterior end of cylinder 12. By axially rotating the insert when tab 42 is either proximate expanded slot segment 38 or 40, the insert is rotated about its longitudinal axis to position one end of wing 54 within the expanded slot segment. By slightly twisting the tab, the end of the wing can be made to protrude the respective expanded slot segment. Further axial rotation of the insert and commensurate depression of the cylinder along one side of the slot will permit one half of the wing to extend over the lateral edge of the expanded slot. Thereafter, the opposite wing can be popped radially outwardly and over the opposed cylindrical surface adjacent the expanded slot. By rotating insert 14 in the opposite direction, ridges 56,58 and 60,62 can be brought into alignment with slot 36 and upon such alignment, leaf spring 44 will spring radially outwardly to its quiescent position. Rectilinear translation of the insert with respect to the cylinder can now readily be effected. While disengagement of the insert from the cylinder can be accomplished by essentially reversing the above discussed procedure, such disengagement must be a very deliberate and affirmative act and is likely to result in breakage. Accordingly, during normal use of holder 10, disengagement cannot and will not come about. Test results indicate that a pulling force in the range of 25 to 40 pounds is required to disengage shield 14 from cylinder 12 due to the interference between tab 42 and finger flange 34. State of the art related blood collection tube holders come apart and expose the double ended needle upon application of a two-thirds or less pulling force. One may therefore conclude that inadvertent detachment of the insert from the cylinder will not occur during any expected use of holder 10.

Holder 10 is intended to be used with commercially available sterilized double ended needles of standard configuration. The procedure attendant venipuncture does not require sterilization of holder 10. Accordingly, sterilization of a holder being manufactured may be avoided. Furthermore, since the holder does not have to be sterilized nor maintained sterile, the handling of the holder in a physician's office, clinic or hospital will require no new or different procedures. The use of holder 10 permits employment of standard venipuncture procedures except for one small modification. At the venipuncture site or shortly thereafter and before the medical personnel releases the holder, tab 42 is translated by a very simple convenient thumb motion to retract the anterior needle. Thereafter, the holder may be immediately disposed of or placed on a tray for later disposal or reuse, all without creating a danger of inadvertent needle stick. The very compact size of being essentially not much longer than a standard double ended needle substantially reduces storage space requirements both prior to and during a venipuncture procedure. Furthermore, the minimal size lessens the space required of containers for disposables. The dimensions of the holder permit use of short blood collection tubes and all size commercially available double ended needles. Aside from the above discussed methods for capping or disposing the double ended needle, other methods may be exercised. While the anterior needle is exposed after use, the anterior needle may be inserted into its original cap or shield lying on a support surface. An upward hooking motion of the holder will cause the cap to slide onto the needle. Thereafter, the cap may be frictionally engaged with the needle hub to maintain the cap in place. To separate the double ended needle from the holder, the cap is turned to unthread the needle engagement between the hub and the boss of the insert and the double ended needle is withdrawn. Secondly, certain bio hazard containers include a clamp like device for gripping objects. The exposed anterior needle may be clamped in the bio hazard container and thereafter disengaged from the holder by turning the holder to unthread the needle hub from the insert. Alternatively, if the configuration of cylinder 12 permits exteriorization of the needle hub from collar 30, the needle hub may be gripped by the bio hazard device and twisted to disengage the double ended needle from the holder.

While the principles of the invention have now been made clear in an illustrative embodiment, there will be immediately obvious to those skilled in the art many modifications of structure, arrangement, proportions, elements, materials and components used in the practice of the invention which are particularly adapted for specific environments and operating requirements without departing from those principles.

We claim:

1. A blood collection tube holder for use with a detachably attached double ended needle having a hub from which hub extends an anterior needle and a posterior needle, said holder comprising in combination:
   a) a cylinder for shielding the anterior needle against inadvertent needle stick after a venipuncture procedure, said cylinder having a first anterior open end in communication with the interior of said cylinder and an inner cylindrical wall;
   b) a cylindrical insert telescopingly engageable with said cylinder for shielding the posterior needle against inadvertent needle stick and for axially translating the anterior needle relative to said cylinder to expose the anterior needle through said first anterior open end and to shield the anterior needle within said cylinder, said insert having an open end for removably receiving at least a part of a blood collection tube and a second anterior open end having means for engaging the hub of the double ended needle to position the posterior needle within said insert to penetrably engage the blood collection tube and to position the anterior needle exterior of and extending from said insert;
   c) a longitudinally extending slot disposed along said cylinder;
   d) tab means unitary with and extending from said insert for engaging said slot to translate and retain the anterior needle between an exposed position external to said cylinder and a shielded position internal to said cylinder;
   e) first detent means for positionally retaining said tab means relative to said slot to define the exposed position of the anterior needle and second detent means for positionally retaining said tab means relative to said slot to define the shielded position of the anterior needle; and
   f) means for preventing disassembly of said insert from within said cylinder, said preventing means comprising wing means for precluding translation of said tab radially inwardly through said slot and through each of said first and second detent means to a location completely within the inner wall of said cylinder, said wing means having a lateral dimension greater than the lateral dimension of any of said slot and said first and second detent means and a longitudinal dimension less than the lateral dimension of said wing means to preclude translation of said wing means radially inwardly through any of said slot and said first and second detent means.

2. The apparatus as set forth in claim 1 wherein the double ended needle includes a cap removably mounted on the hub for capping the anterior needle and wherein said first anterior open end is sized to accommodate insertion and removal of the double ended needle with the cap mounted thereon.

3. The apparatus as set forth in claim 2 wherein said first anterior open end is sized to accommodate manually turning the cap and including means for threadedly engaging and disengaging the hub with said boss.

4. The apparatus as set forth in claim 1 including means for repositioning said tab means along a radial of said insert.

5. The apparatus as set forth in claim 4 including means for biasing said tab means against inward radial repositioning of said tab means.

6. The apparatus as set forth in claim 5 wherein said biasing means comprises an anteriorly extending leaf spring for supporting said tab proximate the anterior end.

7. The apparatus as set forth in claim 1 including means for limiting wobble of said insert relative to said cylinder upon positioning of said insert at the posterior most position relative to said cylinder.

8. A blood collection tube holder for use with a detachably attached double ended needle having a threaded hub from which hub extends an anterior needle and a posterior needle, said holder comprising in combination:
   a) a cylinder for shielding the anterior needle against inadvertent needle stick after a venipuncture procedure, said cylinder having an open end and a necked down end defining a collar having a passageway extending therethrough in communication with the interior of said cylinder;
   b) a cylindrical insert telescopingly engagable with said cylinder for shielding the posterior needle against inadvertent needle stick and for axially translating the anterior needle relative to said cylinder to expose the anterior needle through said passageway and to shield the anterior needle within said cylinder, said insert having an open end for removably receiving at least a part of a blood collection tube and a necked down end having an internally threaded boss for engaging the threaded hub of the double ended needle to position the posterior needle within said insert for penetrably engaging the blood collection tube and to position the anterior needle exterior of and extending from said insert;

c) a longitudinally extending slot disposed along said cylinder;

d) tab means extending from said insert for engaging said slot to translate and retain the anterior needle between an exposed position external to said cylinder and a shielded position internal to said cylinder;

e) means for limiting wobble of said insert relative to said cylinder upon positioning of said insert at the posterior most position relative to said cylinder, said limiting means including a plurality of anteriorly tapered ridges extending radially inwardly from the posterior inner surface of said cylinder; and f) first detent means for positionally retaining said tab means relative to said slot to define the exposed position of the anterior needle and the contained position of said insert within said cylinder and second detent means for positionally retaining said tab means relative to said slot to define the shielded position of the anterior needle and the extended position of said insert posteriorly from said cylinder.

9. The apparatus as set forth in claim 1 wherein the axial length of aid insert is sufficient to enclose the posterior needle and insufficient to extend beyond the posterior end of said cylinder upon retention of said tab means by said first detent means.

10. The apparatus as set forth in claim 9 including means for posteriorly positioning said insert to accommodate access to a pediatric blood collection tube used with said holder.

11. The apparatus as set forth in claim 1 wherein the axial length of said cylinder is sufficient to enclose the anterior needle upon retention of said tab means by said second detent means.

12. The apparatus as set forth in claim 1 wherein the axial length of said cylinder is sufficient to prevent exteriorization of the hub from said boss upon retention of said tab means by said first detent means.

13. The apparatus as set forth in claim 1 including means for maintaining the anterior needle coincident with the longitudinal axis of said cylinder during translation of said insert relative to said cylinder.

14. The apparatus as set forth in claim 1 wherein said first and second detent means comprises first and second expanded slot segments of greater circumferential width than said slot and said tab means includes a base having a circumferential width essentially coincident with that of said first and second expanded slot segments for alternatively penetrably engaging said first and second expanded slot segments and a pedestal extending radially from said base for translation within and along said slot.

15. The apparatus as set forth in claim 14 wherein said tab means includes a wing extending from each side of said pedestal for assisting in manual gripping of said tab means.

16. The apparatus as set forth in claim 15 wherein said wing extends beyond the opposed lateral sides of said first and second expanded slot segments to discourage inward radial disengagement of said tab means from said first and second expanded slot segments.

17. A blood collection tube holder for use with a detachably attached double ended needle having a threaded hub from which hub extends an anterior needle and a posterior needle, said holder comprising in combination:

a) a cylinder for shielding the anterior needle against inadvertent needle stick after a venipuncture procedure, said cylinder having an open end and a necked down end defining a collar having a passageway extending therethrough in communication with the interior of said cylinder;

b) a cylindrical insert telescopingly engagable with said cylinder for shielding the posterior needle against inadvertent needle stick and for axially translating the anterior needle relative to said cylinder to expose the anterior needle through said passageway and to shield the anterior needle within said cylinder, said insert having an open end for removably receiving at least a part of a blood collection tube and a necked down end having an internally threaded boss for engaging the threaded hub of the double ended needle to position the posterior needle within said insert for penetrably engaging the blood collection tube and to position the anterior needle exterior of and extending from said insert;

c) a longitudinally extending slot disposed along said cylinder;

d) tab means extending from said insert for engaging said slot to translate and retain the anterior needle between an exposed position external to said cylinder and a shielded position internal to said cylinder; and e) first detent means for positionally retaining said tab means relative to said slot to define the exposed position of the anterior needle and the contained position of said insert within said cylinder and second detent means for positionally retaining said tab means relative to said slot to define the shielded position of the anterior needle and the extended position of said insert posteriorly from said cylinder, said first and second detent means comprising first and second expanded slot segments of greater circumferential width than said slot and said tab means including a base having a circumferential width essentially coincident with that of said first and second expanded slot segments for alternatively penetrably engaging said first and second expanded slot segments, a pedestal extending radially from said base for translation within and along said slot, a wing extending from each side of said pedestal for assisting in manual gripping of said tab means, said wing extending beyond the opposed lateral sides of said first and second expanded slot segments to discourage inward radial disengagement of said tab means from said first and second expanded slot segments and means disposed proximate said second detent means for restricting access to said wing upon placement of said tab means within said second expanded slot segment.

18. The apparatus as set forth in claim 1 including means for preventing repositioning of said tab means from said second detent means.

19. The apparatus as set forth in claim 1 including means for preventing exteriorization of the anterior needle after it has been drawn into said cylinder.

20. A blood collection tube holder for use with a detachably attached double ended needle having a threaded hub from which hub extends an anterior needle and a posterior needle, said holder comprising in combination:
   a) a cylinder for shielding the anterior needle against inadvertent needle stick after a venipuncture procedure, said cylinder having an open end and a necked down end defining a collar having a passageway extending therethrough in communication with the interior of said cylinder;
   b) a cylindrical insert telescopingly engagable with said cylinder for shielding the posterior needle against inadvertent needle stick and for axially translating the anterior needle relative to said cylinder to expose the anterior needle through said passageway and to shield the anterior needle within said cylinder, said insert having an open end for removably receiving at least a part of a blood collection tube and a necked down end having an internally threaded boss for engaging the threaded hub of the double ended needle to position the posterior needle within said insert for penetrably engaging the blood collection tube and to position the anterior needle exterior of and extending from said insert;
   c) a longitudinally extending slot disposed along said cylinder;
   d) a flexible resilient arm extending from a posterior fixed end in said cylindrical insert to an anterior free end of said arm in said insert, a tab means integrally part of and extending radially outwardly from the anterior free end of said arm for engaging said slot and for guiding said insert upon relative translational movement between said insert and said cylinder;
   e) first detent means for positionally retaining said tab means relative to said slot to define the exposed position of the anterior needle and the contained position of said insert within said cylinder and second detent means for positionally retaining said tab means relative to said slot to define the shielded position of the anterior needle and the extended position of said insert posteriorly from said cylinder; and
   f) means for preventing disassembly of said insert from within said cylinder, said preventing means comprising means for precluding translation of said tab radially inwardly through said slot and through each of said first and second detent means to a location completely within the inner wall of said cylinder.

21. A blood collection tube holder for use with a detachably attached double ended needle having a threaded hub from which hub extends an anterior needle and a posterior needle, said holder comprising in combination:
   a) a cylinder for shielding the anterior needle against inadvertent needle stick after a venipuncture procedure, said cylinder having an open end and a necked down end defining a collar having a passageway extending therethrough in communication with the interior of said cylinder;
   b) a cylindrical insert telescopingly engagable with said cylinder for shielding the posterior needle against inadvertent needle stick and for axially translating the anterior needle relative to said cylinder to expose the anterior needle through said passageway and to shield the anterior needle within said cylinder, said insert having an open end for removably receiving at least a part of a blood collection tube and a necked down end having an internally threaded boss for engaging the threaded hub of the double ended needle to position the posterior needle within said insert for penetrably engaging the blood collection tube and to position the anterior needle exterior of and extending from said insert;
   c) a longitudinally extending slot disposed along said cylinder;
   d) tab means unitary with and extending outwardly from said insert for engaging said slot and for guiding said insert upon relative translational movement between said insert and said cylinder;
   e) a finger flange extending radially outwardly from a posteriorly oriented location on said cylinder, said finger flange including an opening extending therethrough for accommodating passage of said tab means;
   f) first detent means for positionally retaining said tab means relative to said slot to define the exposed position of the anterior needle and the contained position of said insert within said cylinder and second detent means for positionally retaining said tab means relative to said slot to define the shielded position of the anterior needle and the extended position of said insert posteriorly from said cylinder; and
   g) means for preventing disassembly of said insert from within said cylinder, said preventing means comprising means for precluding translation of said tab radially inwardly through said slot and through each of said first and second detent means to a location completely within the inner wall of said cylinder.

22. The apparatus as set forth in claim 21 including means for limiting wobble of said insert relative to said cylinder upon positioning of said insert at the posterior most position relative to said cylinder.

23. The apparatus as set forth in claim 21 wherein said opening includes an arch and including means for bearing against said arch upon positioning said insert in the anterior needle shielded position.

24. A blood collection tube holder for use with a detachably attached double ended needle having a threaded hub from which hub extends an anterior needle and a posterior needle, said holder comprising in combination:
   a) a cylinder for shielding the anterior needle against inadvertent needle stick after a venipuncture procedure, said cylinder having an open end and a necked down end defining a collar having a passageway extending therethrough in communication with the interior of said cylinder;
   b) a cylindrical insert telescopingly engagable with said cylinder for shielding the posterior needle against inadvertent needle stick and for axially translating the anterior needle relative to said cylinder to expose the anterior needle through said passageway and to shield the anterior needle within said cylinder, said insert having an open end for removably receiving at least a part of a blood collection tube and a necked down end having an internally threaded boss defining a passageway for engaging the threaded hub of the double ended needle to position the posterior needle within said insert for penetrably engaging the blood collection tube and to position the anterior needle exterior of and extending from said insert;

c) a longitudinally extending slot disposed along said cylinder;

d) tab means extending from said insert for engaging said slot to translate and retain the anterior needle between an exposed position external to said cylinder and a shielded position internal to said cylinder;

e) means for maintaining the anterior needle coincident with the longitudinal axis of said cylinder during translation of said insert relative to said cylinder, said maintaining means including an annular ridge segment disposed at the anterior end of said insert for bearing against the interior surface of said cylinder; and f) first dent means for positionally retaining said tab means relative to said slot to define the exposed position of the anterior needle and the contained position of said insert within said cylinder and second detent means for positionally retaining said tab means relative to said slot to define the shielded position of the anterior needle and the extended position of said insert posteriorly from said cylinder.

25. A blood collection tube holder for use with a detachably attached double ended needle having a threaded hub from which hub extends an anterior needle and a posterior needle, said holder comprising in combination:

a) a cylinder for shielding the anterior needle against inadvertent needle stick after a venipuncture procedure, said cylinder having an open end and a necked down end defining a collar having a passageway extending therethrough in communication with the interior of said cylinder;

b) a cylindrical insert telescopingly engagable with said cylinder for shielding the posterior needle against inadvertent needle stick and for axially translating the anterior needle relative to said cylinder to expose the anterior needle through said passageway and to shield the anterior needle within said cylinder, said insert having an open end for removably receiving at least a part of a blood collection tube and a necked down end having an internally threaded boss for engaging the threaded hub of the double ended needle to position the posterior needle within said insert for penetrably engaging the blood collection tube and to position the anterior needle exterior of and extending from said insert;

c) a longitudinally extending slot disposed along said cylinder;

d) tab means extending from said insert for engaging said slot to translate and retain the anterior needle between an exposed position external to said cylinder and a shielded position internal to said cylinder;

e) first detent means for positionally retaining said tab means relative to said slot to define the exposed position of the anterior needle and the contained position of said insert within said cylinder and second detent means for positionally retaining said tab means relative to said slot to define the shielded position of the anterior needle and the extended position of said insert posteriorly from said cylinder, said first and second detent means comprising first and second expanded slot segments of greater circumferential width than said slot and said tab means including a base having a circumferential width essentially coincident with that of said first and second expanded slot segments for alternatively penetrably engaging said first and second expanded slot segments, a pedestal extending radially from said base for translation within and along said slot, a wing extending from each side of said pedestal for assisting in manual gripping of said tab means; and f) means extending outwardly from said insert for engaging said slot and for guiding said insert upon relative translational movement between said insert and said slot, a finger flange extending radially outwardly from a posteriorly oriented location on said cylinder, said finger flange including an opening extending therethrough for accommodating passage of said slot engaging means, said opening being sized inadequate to accommodate translation posteriorly of said wing therethrough whereby the interference between said wing and said finger flange locks said insert with said cylinder.

26. A blood collection tube holder for use with a detachably attached double ended needle having a threaded hub from which hub extends an anterior needle and a posterior needle, said holder comprising in combination:

a) a cylinder for shielding the anterior needle against inadvertent needle stick after a venipuncture procedure, said cylinder having an open end and a necked down end defining a collar having a passageway extending therethrough in communication with the interior of said cylinder;

b) a cylindrical insert telescopingly engagable with said cylinder for shielding the posterior needle against inadvertent needle stick and for axially translating the anterior needle relative to said cylinder to expose the anterior needle through said passageway and to shield the anterior needle within said cylinder, said insert having an open end for removably receiving at least a part of a blood collection tube and a necked down end having an internally threaded boss for engaging the threaded hub of the double ended needle to position the posterior needle within said insert for penetrably engaging the blood collection tube and to position the anterior needle exterior of and extending from said insert;

c) a longitudinally extending slot disposed along said cylinder;

d) tab means extending from said insert for engaging said slot to translate and retain the anterior needle between an exposed position external to said cylinder and a shielded position internal to said cylinder;

e) first detent means for positionally retaining said tab means relative to said slot to define the exposed position of the anterior needle and the contained position of said insert within said cylinder and second detent means for positionally retaining said tab means relative to said slot to define the shielded position of the anterior needle and the extended position of said insert posteriorly from said cylinder; and f) guard means for restricting access to said tab means upon placement of said tab means coincident with said second detent means.

27. The apparatus as set forth in claim 26 wherein said guard means includes a cover and side walls for receiving said tab means.

28. The apparatus as set forth in claim 27 including ramp means disposed adjacent said slot and extending radially outwardly posteriorly, said ramp means including a butt end terminating proximate said second detent means.

29. The apparatus as set forth in claim 28 wherein said ramp means comprises a ramp disposed on opposed sides of said slot.

30. A blood collection tube holder for use with a detachably attached double ended needle having a threaded hub from which hub extends an anterior needle and a posterior needle, said holder comprising in combination:
 a) a cylinder for shielding the anterior needle against inadvertent needle stick after a venipuncture procedure, said cylinder having an open end and a necked down end defining a collar having a passageway extending therethrough in communication with the interior of said cylinder;
 b) a cylindrical insert telescopingly engagable with said cylinder for shielding the posterior needle against inadvertent needle stick and for axially translating the anterior needle relative to said cylinder to expose the anterior needle through said passageway and to shield the anterior needle within said cylinder, said insert having an open end for removably receiving at least a part of a blood collection tube and a necked down end having an internally threaded boss for engaging the threaded hub of the double ended needle to position the posterior needle within said insert for penetrably engaging the blood
 d) tab means unitary with and extending outwardly from said insert for engaging said slot and for guiding said insert upon relative translational movement between said insert and said cylinder;
 e) a finger flange extending radially outwardly from a posteriorly oriented location on said cylinder, said finger flange including an opening extending therethrough for accommodating passage of said tab means;
 f) first detent means for positionally retaining said tab means relative to said slot to define the exposed position of the anterior needle and the contained position of said insert within said cylinder and second detent means for positionally retaining said tab means relative to said slot to define the shielded position of the anterior needle and the extended position of said insert posteriorly from said cylinder; and
 g) means for preventing disassembly of said insert from within said cylinder, said preventing means comprising means for precluding translation of said tab radially inwardly through said slot and through each of said first and second detent means to a location completely within the inner wall of said cylinder.

31. A method using a blood collection tube holder having an insert axially translatable therewithin for preventing inadvertent needle stick during a blood collection procedure by either needle of a double ended blood collection needle having a threaded hub threadedly engageable with the insert, said method comprising the steps of:
 a) upon completion of venipuncture, retracting the anterior needle of the double ended needle into a cylinder of the holder by posteriorly translating the insert at least initially completely within the cylinder, which insert is threadedly engaged with the threaded hub;
 b) positioning the insert in a first dent position relative to the cylinder during venipuncture prior to said step of retracting and in a second detent position relative to the cylinder during said step of retracting to draw the anterior needle into the cylinder, said step of positioning including the step of translating a tab integral with and extending from the insert through a longitudinally aligned slot disposed in the cylinder, which tab includes a unitary wing, which wing has a lateral dimension greater than the lateral dimension of any of the slot and the first and second detents and a longitudinal dimension equivalent to or less than the longitudinal dimension of at least one of the slot and the first and second detents and which wing is located radially outwardly of the cylinder to preclude inward radial movement of the tab past the sides of the slot;
 c) inserting an anterior needle cap partially into the cylinder to receive therein the anterior needle and to grippingly engage the hub;
 d) rotating the anterior needle cap to unthread and disengage the hub from the insert; and
 e) withdrawing the anterior needle cap and the gripped double ended needle from the cylinder.

32. The method as set forth in claim 31 including the step of maintaining the posterior needle within and shielded by the insert prior to and subsequent to exercise of said retracting step to prevent inadvertent needle stick by the posterior needle.

33. The method as set forth in claim 32 including the step of preventing repositioning of the insert from the second detent position.

34. The method as set forth in claim 31 including the step of inserting the posterior needle and the hub into the cylinder and threadedly engaging the threaded hub with the insert prior to exercise of said step of retracting.

35. The method as set forth in claim 34 wherein the anterior needle is shielded by a hub supported cap prior to exercise of said inserting step and including the step of withdrawing the cap shielding the anterior needle to expose the anterior needle on completion of said step of threadedly engaging.

36. The method as set forth in claim 31 including the step of accommodating insertion of the posterior needle of the double ended needle, the hub and at least a part of the anterior needle into the cylinder while an anterior needle cap remains in gripping engagement with the threaded hub.

37. The method as set forth in claim 36 including the step of withdrawing from within the cylinder only the anterior needle cap after the threaded hub has become threadedly engaged with the insert.

38. The method as set forth in claim 31 wherein the cylinder and the insert include longitudinal axes and including the step of maintaining alignment of the longitudinal axis of the insert with the longitudinal axis of the cylinder during translation of the insert relative to the cylinder.

39. The method as set forth in claim 31 including the step of preventing relocation of the tab from the second detent position to the first detent position.

40. The method as set forth in claim 31 including the step of preventing dislocation of the tab from the first detent position due to the forces imposed during venipuncture.

41. The method as set forth in claim 31 including the step of forcing the tab radially inwardly of the insert to dislocate the tab from each of the first and second detent positions.

42. The method as set forth in claim 41 including the step of preventing access to the tab and the ability to force the tab radially inwardly when the tab is in the second detent position.

43. The method as set forth in claim 31 including the step of preventing exteriorization of the anterior needle by preventing translation of the insert on completion of said step of retracting.

44. The method as set forth in claim 31 including the step of locking the insert with the cylinder to prevent inadvertent disengagement between the insert and the cylinder.

45. The method as set forth in claim 31 including the step of translating the tab over the butt end of ramp means and into the second detent position and establishing an interference between the tab and the butt end to prevent relocation of the tab.

46. The method as set forth in claim 31 including the step of shielding the tab in the first detent position with sidewalls disposed on opposed sides of the first detent position.

47. A method using a blood collection tube holder having an insert axially translatable therewithin for preventing inadvertent needle stick during a blood collection procedure by either the anterior or the posterior needle of a double ended blood collection needle having a threaded hub threadedly engageable with the insert and a cap secured to the hub for shielding the anterior needle, said method comprising the steps of:
  a) inserting the posterior needle, hub and part of the cap shielded anterior needle through an apertured end of a cylinder of the holder;
  b) during said step of inserting, penetrably engaging a threaded boss at one end of the insert translatably disposed completely within the length of the cylinder with the posterior needle and threading the threaded hub with the threaded boss to support the double ended needle;
  c) disengaging the cap from the threaded hub;
  d) withdrawing the cap through the apertured end of the cylinder to expose the anterior needle; and
  e) positioning the insert in a first detent position relative to the cylinder during the blood collection procedure and in a second detent position relative to the cylinder to draw the anterior needle into the cylinder, said step of positioning including the step of translating a tab integral with and extending from the insert through a longitudinally aligned slot disposed in the cylinder which tab includes a unitary wing, which wing has a lateral dimension greater than the lateral dimension of any of the slot and the first and second detents and a longitudinal dimension equivalent to or less than the longitudinal dimension of at least one of the slot and the first and second detents and which wing is located radially outwardly of the cylinder to preclude inward radial movement of the tab past the sides of the slot and the first and second detents.

48. The method as set forth in claim 47 including the step of translating the insert posteriorly relative to the cylinder to retract the anterior needle into the cylinder while the posterior needle is contained within the insert.

49. The method as set forth in claim 48 including the step of locking the insert in the second detent position relative to the cylinder on completion of said step of translating to prevent exteriorization of the anterior needle.

50. The method as set forth in claim 49 including the step of urging the insert anteriorly relative to the cylinder and into the first detent position to exteriorize the anterior needle prior to exercise of said step of translating and in preparation for preforming a blood collection procedure.

51. The method as set forth in claim 47 including the step of urging the insert anteriorly relative to the cylinder and into the first detent position to exteriorize the anterior needle prior to exercise of said step of translating and in preparation for performing a blood collection procedure.

52. The method as set forth in claim 49 including the step of preventing posterior translation of the insert subsequent to exercise of said locking step without breakage of the insert and the cylinder.

53. The method as set forth in claim 47 including the step of penetrably inserting the anterior needle into the cap on completion of the venipuncture procedure.

54. The method as set forth in claim 47 including the step of inserting and clamping the anterior needle in a bio hazard container on completion of the venipuncture procedure.

55. A method for assembling a cylinder having a longitudinal axis and a posterior opening and an insert to obtain a blood collection tube holder for shielding a double ended needle therewithin subsequent to a venipuncture procedure and wherein the cylinder includes an axially extending slot terminated anteriorly at a first detent position by a first expanded slot segment having a terminal anterior end and terminated posteriorly at a second detent position by a second expanded slot segment having a terminal posterior end and wherein the insert includes a tab unitary with the insert extending radially outwardly proximate the anterior end of the insert and mounted upon a flexible resilient arm extending from a posterior fixed end in said cylindrical insert to an anterior free end of said arm in said insert to accommodate inward radial movement which tab includes a base dimensioned for engagement with either of the first and second expanded slot segments, a pedestal translatable within the slot in response to relative axial displacement between the cylinder and the insert and a wing formed unitary with the pedestal and having opposed ends extending in opposed directions from the pedestal and radially outward of the cylinder a distance sufficient to extend beyond the opposed axial sides of each of the first and second expanded slot segments, said method comprising the steps of:
  a) depressing the arm of the insert to radially inwardly displace the tab;
  b) sliding the anterior end of the insert and the inwardly displaced tab into the posterior opening of the cylinder;
  c) rotating the insert axially relative to the longitudinal axis of the cylinder to locate one end of the wing in penetrating engagement with any of the first and second expanded slot segments and the axially extending slot and in overlapping relationship with an axially aligned edge of any of the penetrated expanded slot segments and the axially extending slot;

d) exteriorizing the other end of the wing past the opposed axially aligned edge of the penetrated expanded slot segment; and e) penetrably positioning the pedestal in the slot by repositioning the insert relative to the cylinder.

56. The method as set forth in claim 55 including the step of limiting radial inward movement of the arm by engaging the wing with the cylinder to prevent disengagement of the tab from the cylinder.

57. A blood collection tube holder for use with a detachably attached double ended needle having a hub from which hub extends an anterior needle and a posterior needle, said holder comprising in combination:

a) a cylinder for shielding the anterior needle against inadvertent needle stick after a venipuncture procedure, said cylinder having a posterior open end and an anterior end defining a collar having a passageway extending therethrough in communication with the interior of said cylinder;

b) a cylindrical insert telescopingly engagable with said cylinder for shielding the posterior needle against inadvertent needle stick and for axially translating the anterior needle relative to said cylinder to expose the anterior needle through said passageway and to shield the anterior needle within said cylinder, said insert having a posterior open end for removably receiving at least a part of a blood collection tube and an anterior and having a boss for engaging the hub of the double ended needle to position the posterior needle within said insert for penetrably engaging the blood collection tube and to position the anterior needle exterior of and extending from said insert;

c) a longitudinally extending slot disposed along said cylinder; and d) tab means unitary with and extending outwardly from said insert for engaging said slot and for translating along said slot to guide said insert upon relative translational movement between said insert and said cylinder, including wing means disposed radially outwardly of said cylinder for preventing movement of said tab means radially inwardly of said cylinder, said wing means having a longitudinal dimension and a lateral dimension greater than each of the longitudinal dimension of said wing means and the width of said slot to prevent the radial movement of said wing means inwardly of said cylinder.

58. A blood collection tube holder for use with a detachably attached double ended needle having a hub from which hub extends an anterior needle and a posterior needle, said holder comprising in combination:

a) a cylinder for shielding the anterior needle against inadvertent needle stick after a venipuncture procedure, said cylinder having an anterior open end in communication with the interior of said cylinder and an inner cylindrical wall;

b) a cylindrical insert telescopingly engagable with said cylinder for shielding the posterior needle against inadvertent needle stick and for axially translating the anterior needle relative to said cylinder to expose the anterior needle through said anterior open end and to shield the anterior needle within said cylinder, said insert having a posterior open end for removably receiving at least a part of a blood collection tube and an anterior open end having means for engaging the hub of the double ended needle to position the posterior needle within said insert to penetrably engage the blood collection tube and to position the anterior needle exterior of and extending from said insert;

c) a longitudinally extending slot disposed along said cylinder;

d) tab means extending from said insert for engaging said slot to translate and retain the anterior needle between an exposed position external to said cylinder and a shielded position internal to said cylinder;

e) first detent means for positionally retaining said tab means relative to said slot to define the exposed position of the anterior needle and second detent means for positionally retaining said tab means relative to said slot to define the shielded position of the anterior needle; and f) said tab means including a leaf spring extending from said insert and ridge means extending from said leaf spring for engaging said slot upon retention of said tab means with each of said first and second detent means to prevent rotation of said insert relative to said cylinder.

59. The holder as set forth in claim 58 wherein said tab means includes a pedestal extending radially outwardly from said leaf spring and wherein said ridge means extends anteriorly and posteriorly of said pedestal.

60. The holder as set forth in claim 58 wherein said ridge means comprises a pair of parallel ridges for slidingly engaging opposed sides of said slot.

61. A blood collection tube holder for use with a detachably attached double ended needle having a hub from which hub extends an anterior needle and a posterior needle, said holder comprising in combination:

a) a cylinder for shielding the anterior needle against inadvertent needle stick after a venipuncture procedure, said cylinder having an anterior open end in communication with the interior of said cylinder and an inner cylindrical wall;

b) a cylindrical insert telescopingly engagable with said cylinder for shielding the posterior needle against inadvertent needle stick and for axially translating the anterior needle relative to said cylinder to expose the anterior needle through said anterior open end and to shield the anterior needle within said cylinder, said insert having an open end for removably receiving at least a part of a blood collection tube and an anterior open end having means for engaging the hub of the double ended needle to position the posterior needle within said insert to penetrably engaging the blood collection tube and to position the anterior needle exterior of and extending from said insert;

c) a longitudinally extending slot disposed along said cylinder;

d) tab means extending from said insert for engaging said slot to translate and retain the anterior needle between an exposed position external to said cylinder and a shielded position internal to said cylinder;

e) first detent means for positionally retaining said tab means relative to said slot to define the exposed position of the anterior needle and second detent means for positionally retaining said tab means relative to said slot to define the shielded position of the anterior needle;

f) a flange extending radially outwardly from a posteriorly oriented location on said cylinder, said flange including an opening corresponding with a longitudinal extension of said slot and an arch defining the edge of the opening; and g) ridge means disposed upon said insert for bearing against said arch to stabilize said insert relative to said cylinder when said tab means is in engagement with said second detent means.

62. The holder as set forth in claim 61 wherein said ridge means includes ridges extending from said insert for engaging said slot upon engagement of said tab means with each of said first and second detent means to inhibit rotation of said insert relative to said cylinder.

63. The holder as set forth in claim 62 wherein said ridges extends anteriorly and posteriorly from said tab means.

* * * * *